United States Patent [19]
McLoughlin et al.

[11] Patent Number: 5,939,073
[45] Date of Patent: Aug. 17, 1999

[54] FISH PANCREATIC DISEASE VIRUS

[75] Inventors: Marian F. McLoughlin, Belfast; Robert Thomas Nelson, Bangor, both of United Kingdom

[73] Assignee: Akzo Nobel N.V., Arnhem, Netherlands

[21] Appl. No.: 08/544,681

[22] Filed: Oct. 18, 1995

[30] Foreign Application Priority Data

Oct. 18, 1994 [GB] United Kingdom .................... 9420956
Apr. 28, 1995 [GB] United Kingdom .................... 9508704
May 10, 1995 [GB] United Kingdom .................... 9509425

[51] Int. Cl.$^6$ .............................. A61K 39/12; C12N 7/00; C07K 16/10; C12Q 1/70
[52] U.S. Cl. .................................... 424/204.1; 435/235.1; 435/5; 530/389.4; 530/391.1
[58] Field of Search ................... 435/235.1, 5, 252.3, 435/69.3, 240.2, 320.1; 424/130.1, 147.1, 159.1, 204.1, 218.1; 530/350, 857, 855, 389.4, 391.1; 536/23.72

[56] References Cited

U.S. PATENT DOCUMENTS 5,165,925  11/1992  Leong .................................. 424/186.1

OTHER PUBLICATIONS

R.T. Nelson et al., *Disease of Aquatic Organisms*, 22:25–32, 1995.
M. McLoughlin, *Fish Farmer Magazine*, 18:2:19, 1995.
A.H. McVicar, *Aquaculture*, 67:71–78, 1987.
A.H. McVicar, *Bull. Eur. Fish. Pathol.*, 10(3):84–87, 1990.
R.S. Raynard, *Diseases of Aquatic Organisms*, 15:123–128, 1993.
M. Murphy et al., *Journal of Fish Diseases*, 1992, 15:401–408.
G. Houghton, *Diseases of Aquatic Organisms*, 18:109–118, 1994.
A.L.S. Munro, *Helgolander Meeresuntersuchungen*, 37:571–586 (1984).
H.W. Ferguson et al., *The Veterinary Record*, 19:297–299, 1986.
H.W. Ferguson et al., *Journal of Fish Diseases*, 1986, 9:95–98.

*Primary Examiner*—Mary E. Mosher
*Assistant Examiner*—Ali R. Salimi
*Attorney, Agent, or Firm*—Mary E. Gormley

[57] ABSTRACT

There is described a novel virus which is the causative agent of fish pancreatic disease, which is a serious disease affecting Atlantic salmon. A method of isolating the virus through co-cultivation of infected tissues following by passage is described and an isolated strain of the virus has been deposited. The use of the virus, or proteins or polypeptide derived therefrom as a vaccine or in diagnosis is described, together with genetically engineered constructs.

13 Claims, 5 Drawing Sheets

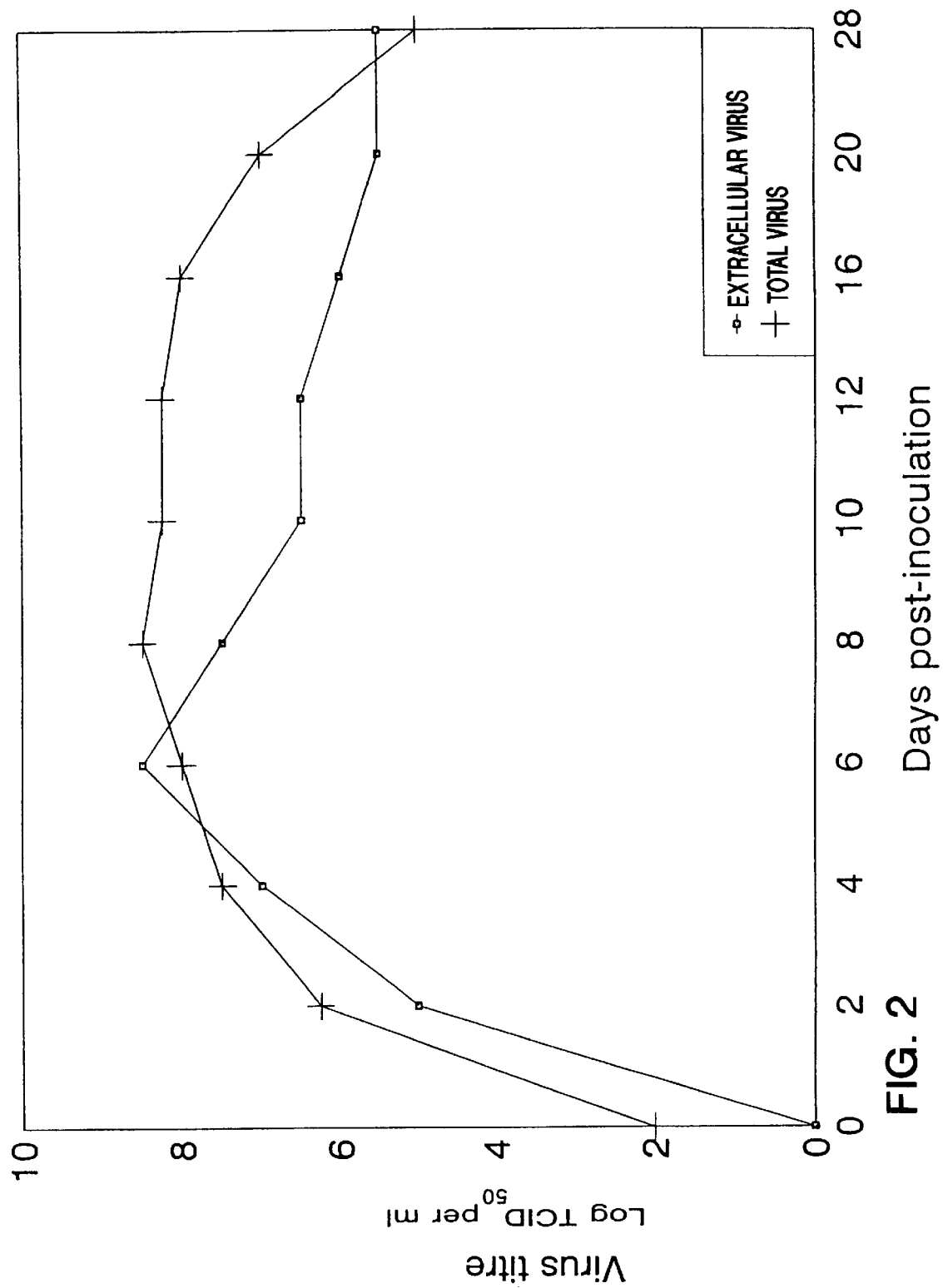

FISH PANCREATIC DISEASE VIRUS

FIELD OF THE INVENTION

There is provided a novel virus which is a causative agent of fish pancreas disease. The virus may be used to provide a vaccine and/or a method of diagnosis of the disease.

BACKGROUND OF THE INVENTION

Pancreas Disease (PD) is a serious disease affecting Atlantic salmon (*Salmon salar L*). The disease causes lesions in the pancreas, including loss of pancreatic exocrine tissue and fibrosis, cardiac and skeletal muscle myopathies. It is believed that other salmonoid species, such as rainbow trout, wild Atlantic salmon, could also be infected by PD.

Outbreaks of PD were first described in 1984 by Munro et al, in Helgoland Meeresuntersuchungen 37:571–586 (1984), but PD was recognised as early as 1976. PD has also been reported in all of the major salmon farming countries of the world, including Norway, Ireland, France, Spain and Western U.S.A. (see Kent et al, Bull. Eur. Ass. Fish Path. 7:29–31 (1987); Poppe et al, in Bull. Eur. Ass. Fish Path. 9(4):83–85 (1989); and Raynard et al in Proceedings of a European Commission Workshop, Scottish Office Aquaculture Report No 1, p2–4 (1992)).

PD is known to affect fish in their first year in salt water and to spread rapidly in farmed fish held in sea cages. Ferguson et al (in Journal of Fish Diseases 9:95–98 (1986)) reported that affected fish were thin, anorexic and lethargic with a tendency to congregate in cage corners and to fail to maintain a horizontal position. In addition to the primary pancreatic lesions, Ferguson et al supra reported that fish affected by PD exhibited severe degenerative cardiomyopathy. These observations were confirmed in a later study by Murphy et al (see Journal of Fish Disease 15:401–408 (1992)) who found that cardiac and skeletal myopathy is exacerbated in fish infected with PD.

In Ireland over the period 1988–1992 PD resulted in 15–20% of recorded mortalities in salmon smolts in their first year at sea. The estimated cost to the Irish industry in terms of loss of production is currently thought to be around £25 million per year. The current 1994 production figures for Norway, Scotland and Ireland are as follows:

| Country | Tonnes of salmon produced | Numbers of smolts put to sea |
| --- | --- | --- |
| Norway | 200,000 | 80 million |
| Scotland | 55,000 | 20 million |
| Ireland | 44,000 | 7 million |

McVicar et al postulated that PD was caused by an infectious agent. This proposition is supported by the results of epidemiological studies and transmission experiments by various workers, which suggest an infectious aetiology for the disease, (see McVicar in Aquaculture 67:71–78 (1987); McVicar in Bull. Eur. Ass. Fish Path. 10:84–87 (1990); Raynard et al, Dis. Aquat. Org. 15:123–128 (1993)); and Murphy et al (1992) supra). Recently Houghton (1994) 18: 109–118 reported that fish become resistant to re-infection after inoculation with PD, supporting the notion that PD is caused by an infectious agent. However, to date no infectious agent has been isolated despite numerous attempts to do so (see McVicar (1987) supra; Munro supra; and Murphy supra).

SUMMARY OF THE INVENTION

The present invention reports the isolation of the causative agent of PD for the first time. The causative agent has now been found to be a spherical virus of 65.5±4.3 nm in size, also referred to herein as FPDV virus. Without projections it has a diameter of 46.8±2.5 nm, is chloroform and pH sensitive, resistant to inhibition by BUDR and on examination by electron microscope morphologically possesses similarities to a member of the Togavirus group. The Togavirus family is comprised of 3 genera, Alphaviruses (27 species), Rubiviruses (1 species) and Arteriviruses (1 species). When inoculated into freshwater salmon parr and marine salmon post-smolts it produces pancreas disease with its associated morphological changes in the pancreas, heart, and skeletal muscle.

Viewed from one aspect, the present invention provides Fish Pancreas Disease Virus (FPDV).

FPDV is a toga-like virus. It consists of spherical enveloped particles, having a particle size of 64–66 nm as measured by electron microscopy and a density of 1.2 g/ml in caesium chloride. Inoculation of $10^{3.5}$ $TCID_{50}$ intraperitoneally into Atlantic salmon post-smolts held in sea water at 14° C. causes the fish to develop symptoms of pancreatic disease, that is to become inappetant and to develop pancreatic acinar cell necrosis, cardiac necrosis and skeletal myopathy.

By FPDV we mean a virus having the above characteristics. The invention is not limited to any particular virus strain of FPDV, however embodiments of the invention are directed to the specific strain(s) of FPDV isolated and closely related strains thereof. By "closely related strains" we mean any strain which shares similar genotypic and/or phenotypic characteristics to the strain(s) isolated. In particular this phrase encompasses slightly modified forms of the virus which retain substantially the same functional activities. Thus, for example some amino acid or nucleotide additions, deletions or alterations have very little effect; if any, on the functional activities of the virus.

In particular, with FPDV we mean a fish virus which serologically reacts with convalescent anti-FPDV antiserum or antiserum raised against the deposited FPDV sample (ECACC No. V94090731). More in particular a FPDV is a fish virus which gives a positive reaction with either of these antisera in an indirect fluorescent antibody test (IFA).

Desirably the virus of the present invention is in a form substantially free of other types of viral or microbial material.

A sample of FPDV has been deposited at European Collection of Animal Cell Cultures, Porton Down, Wiltshire, United Kingdom (ECACC) under Deposit No V94090731 on 7th Sep. 1994.

Further, the present invention provides polypeptides derived from FPDV (which term includes functional equivalents or parts of such polypeptides). The term "polypeptide" as used herein is not limiting with regard to the size of the molecule and includes distinctive short peptides as well as large proteins.

The polypeptides of the present invention may be produced by any convenient method. For example, the polypeptides may be produced by harvest from active or attenuated forms of FPDV, including proteolytic treatment of such forms of FPDV. Suitable proteolytic agents are well-known to those skilled in the art, and include enzymes such as trypsin or pepsin and chemical reagents such as sulphuric or hydrochloric acids. It is also possible to use detergents to solubilise virus preparations to produce whole proteins that may be active. Alternatively, the polypeptides of the present invention may be produced by genetic engineering techniques. For example, an appropriate protein-encoding portion of a nucleotide sequence may be expressed to produce the required polypeptide. The required genetic engineering techniques are well-known to those skilled in the art, but in summary a cDNA copy of at least the appropriate portion of the FPDV RNA genome is prepared. Suitable primers for cDNA production may include an oligo T primer, a primer designed from nucleotide information of a related virus or primers which are produced with random sequences. The DNA may then be placed into an appropriate vector and optionally the proteins encoded thereby may be expressed by a compatible host. Optional steps include insertion of a suitable expression control sequence, clonal expansion of the recombinant vector and selection of the required recombinant construct.

As a general reference to genetic engineering techniques, mention may be made of Maniatis et al, in Molecular Cloning a Laboratory Manual, Cold Spring Harbor Laboratory, Cold Spring Harbor, N.Y., 1982.

The polypeptides of the present invention include all polypeptides of FPDV (including functional equivalents or parts thereof) and thus comprises polypeptides having a structural or a non-structural role in the virus particle. With regard to the structural polypeptides of FPDV mention may be made of the core and envelope polypeptides of FPDV. The invention also covers a polypeptide comprising a surface epitope of FPDV. The present invention also covers non-glycosylated and glycosylated forms of the polypeptides.

Viewed from a further aspect, the present invention provides a genetic construct comprising a nucleotide sequence derived from at least part of the genome of FPDV.

Thus the present invention provides a polynucleotide having a nucleotide sequence at least part of which corresponds to a nucleotide sequence derived from at least part of the genome of FPDV, which may include a protein encoding region.

The phrase "derived" from includes identical and complementary copies of at least a part of the genome of FPDV, whether of RNA or DNA and whether in single or double-stranded form. The phrase "derived from" further includes sequences with alterations which (due to the degeneracy of the genetic code) do not affect the amino acid sequence of the polypeptide expressed, as well as sequences modified by deletions, additions or replacements of nucleotide(s) which cause no substantial deleterious effect to function (including the function of the polypeptide expressed).

In particular, the genetic constructs of the present invention encompass the naturally occurring genome of FPDV and cDNA equivalents thereof. Further, the genetic construct of the present invention includes all recombinant constructs comprising nucleotide sequences derived from at least part of the genome of FPDV. Such recombinant constructs may be designed to express only a particular polypeptide or polypeptides of FPDV and may include non-FPDV (foreign) expression control sequences. Alternatively, the recombinant constructs may include an expression control sequence of FPDV, and optionally a non-FPDV (foreign) protein encoding sequence.

In a particular embodiment, the present invention includes a vector (such as a cloning or expression vector) which comprises a genetic construct as defined above. Vectors include conventional cloning and expression plasmids for bacterial and yeast host cells as well as eukaryotic virus vectors such as vaccinia, which may be useful for expression of FPDV proteins in eukaryotic cell lines. Such a vector may be used to transform a suitable host cell (either for cloning or expression purposes) and the transformed host cell also forms a further aspect of the present invention. Suitable host cell types for transformation with FPDV itself include Chinook salmon embryo (CHSE-214) cells, Atlantic salmon cell lines and Rainbow trout cell lines. However, if the vector produced is comprised only in part of a nucleotide sequence derived from FPDV it may be more appropriate to select a host cell type which is compatible with the vector. Mention may be made of prokaryotic host cells such as *E coli* and *Yersinia ruckeri* which have been used successfully for the expression of viral haemorrhagic septicaemia rhabdovirus as well as eukaryotic host cells, including yeasts, algae and fish, insect or mammalian cells in culture. Insect cells may be especially useful where a baculovirus expression system is used. Suitable host cells will be known to those skilled in the art.

In particular, the vector of the present invention may be based upon a genetically engineered version of the FPDV genome, which includes a coding sequence of a non-FPDV polypeptide and is able to express said non-FPDV polypeptide.

The genetic constructs, vectors and transformed host cells may be used to express polypeptides, especially FPDV polypeptides.

The non-FDPV polypeptide may be, for example, a polypeptide from a fish disease causative agent. The vector may thus be useful as a vaccine, the expression of the non-FPDV polypeptide in vector-infected fish inducing an immune response to the fish disease causative agent.

There is evidence that fish acquire a strong immunity to PD after field and experimental exposure (see Raynard et al, Dis Aquat Org 15: 123–128 (1993)). The isolation of FPDV will enable the development of antigen and nucleic acid detection systems which would aid in the rapid diagnosis of PD and assist in more thorough investigation of the pathogenesis and epidemiology of this important fish disease. The genetic constructs and polypeptides of the present invention may therefore be useful to produce a vaccine and/or diagnostic materials against FPDV.

In a yet further aspect, the present invention provides a vaccine to PD, said vaccine comprising FPDV or a polypeptide derived from FPDV (including functional equivalents and parts thereof). In particular FPDV could be used as a vaccine vector, that is could be genetically engineered as an expression vector having particular utility in vaccine production.

Thus the vaccine may be, for example, an attenuated or inactivated form of FPDV itself. Inactivated forms of FPDV may be produced by heating a sample of FPDV, for example heating above 50° C., by treatment with chloroform, adjustment of pH or by any other suitable means. Attenuated forms of FPDV may be produced by prolonged passage of the virus in cell culture, often of a different species, or by growth at progressively higher temperatures, to select populations better adapted to a higher temperature. Development of plaque purification methods to select variants by plaque size has been used in other viruses and may be suitable here. Alternatively the vaccine may comprise a polypeptide of FPDV, preferably a polypeptide which is immunogenic in fish (especially Atlantic salmon), that is to say the polypeptide induces an immune reaction in the fish. Such a polypeptide may be produced by any convenient means, for example by using genetic engineering techniques.

Vaccines to other togaviruses are known in the art and thus the techniques of producing a suitable vaccine are available to the skilled practitioner. Mention may be made to Roerig et al in High Technology Route to Virus Vaccines, ed Driesman, Bronson & Kennedy 1985, Page 142 and also to Leong et al in Annual Review of Fish Diseases (1993) pages 225–240.

A suitable FPDV vaccine or non-FPDV vaccine, using FPDV as an expression vector as described above, could be produced in a manner analogous to Semliki forest virus (SFV). With SFV, the production of a full-length cDNA clone, from which infectious RNA could be transcribed, and the elucidation of SFV molecular biology has facilitated the separation of cDNAs that code for the RNA replication proteins from cDNAs coding for the capsid proteins. A subgenomic mRNA encoding the capsid proteins can be isolated from infected cells. This separation has been exploited to produce "non-replicating" SFV particles comprising the normal virus capsid enclosing an RNA that encodes the RNA replication proteins only. These particles are produced by co-transfecting cells with 2 different RNAs each synthesised by in vitro transcription from distinct cDNAs. Transcript 1 encodes the proteins responsible for RNA replication and transcript 2 codes for the proteins constituting the capsid and envelope. Inside the transfected cell, both RNAs are replicated and translated. Due to its possession of the packaging signal, only the RNA encoding the replication proteins is encapsidated. The incorporation of foreign genes into the cDNA encoding the RNA replication capability has allowed SFV to be exploited as a very efficient expression system. Thus, cells transfected with a modified transcript 1 along will express foreign proteins. The potential of SFV as a vector vaccine is realised when cells are co-transfected with the modified transcript 1 and transcript 2. The outcome in this case is the production of "non-replicating" SFV particles which will infect cells and effectively produce foreign proteins capable of invoking a protective immune response.

Optionally the vaccine would be administered to young fish, for example salmon in the fresh-water stage. The vaccine may be added directly to the water containing the fish. Alternatively, the fish (or a sample of the fish) could be inoculated directly. Where only a sample of the fish are inoculated, immunity may be conferred on the other fish due to the contact with the vaccinated fish.

In another aspect, the present invention provides a diagnostic reagent for PD, said reagent comprising a moiety capable of binding selectively to FPDV or to a component thereof.

Examples of said moiety include antibodies or other proteins able to bind selectively to FPDV itself or to a polypeptide thereof, lectins which bind selectively to FPDV, oligosacharides or glycosylated polypeptides thereof, and polynucleotides having sequences which are complementary to at least a portion of the FPDV genome.

Optionally the diagnostic reagent may include a marker, such as a radioactive label, a chromophore, fluorophore, heavy metal, enzymic label, antibody label or the like. Optionally, the diagnostic reagent may be immobilised (for example on a bead, rod, vessel surface or membrane) and the sample to be tested is brought into direct contact with said diagnostic reagent.

Antibodies specific to FPDV which may be utilised as said moiety in the diagnostic reagent form a further aspect of the present invention If required the antibodies may be monoclonal antibodies.

In a yet further aspect, the present invention provides a method of isolating FPDV. This method comprises identifying fish suffering from PD, preferably fish in the acute stage of PD (as defined by Munro et al, supra). Affected tissues (such as the pancreas or kidney) are co-cultivated with Chinook salmon embryo (CHSE-214) cells for an appropriate length of time, for example up to 35 days, especially approximately 28 days. The co-cultivated cells are then passaged through CHSE cells.

The present invention also provides a method of diagnosing PD, said method comprising the following steps):
 i) contacting a test sample with a diagnostic reagent of the present invention to produce a reagent complex;
 ii) optional washing step; and
 iii) determining the presence, and optionally the concentration, of reagent complex and thus the presence or amount of FPDV in the sample.

The method of diagnosis may be performed on any sample suspected to contain FPDV. For example, tissue samples (for example kidney, spleen, heart, pancreas, liver, gut or blood) of the fish may be subjected to the diagnosis procedure. Generally, it is preferred for a blood sample to be tested, thus providing a non-fatal diagnosis. It may also be possible for the diagnostic test to be performed on a sample of the water which has been used to contain the fish.

The present invention also provides a method of producing FPDV and a method of producing a polypeptide derived from FPDV.

BRIEF DESCRIPTION OF THE DRAWINGS

The figures of the Application may be briefly discussed as follows:

FIG. 2. Growth of SPDV in CHSE-214 cells.

Figure 5:
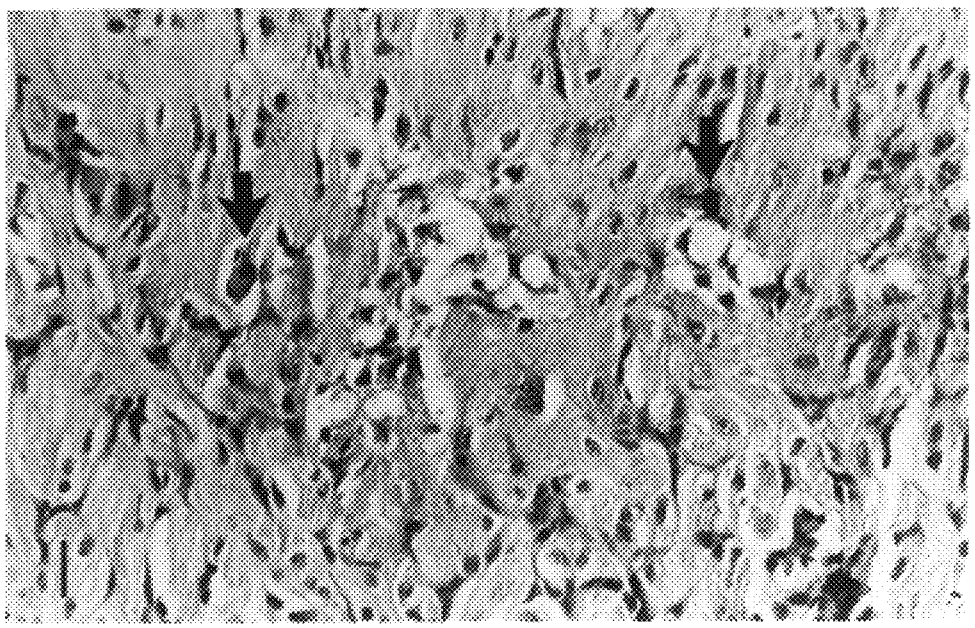

Bar=50 μm;

FIG. 5: Multifocal cardiomyocytic necrosis which occurred concurrently with the pancreatic lesions at post-inoculation day 21 (→)

Figure 6:
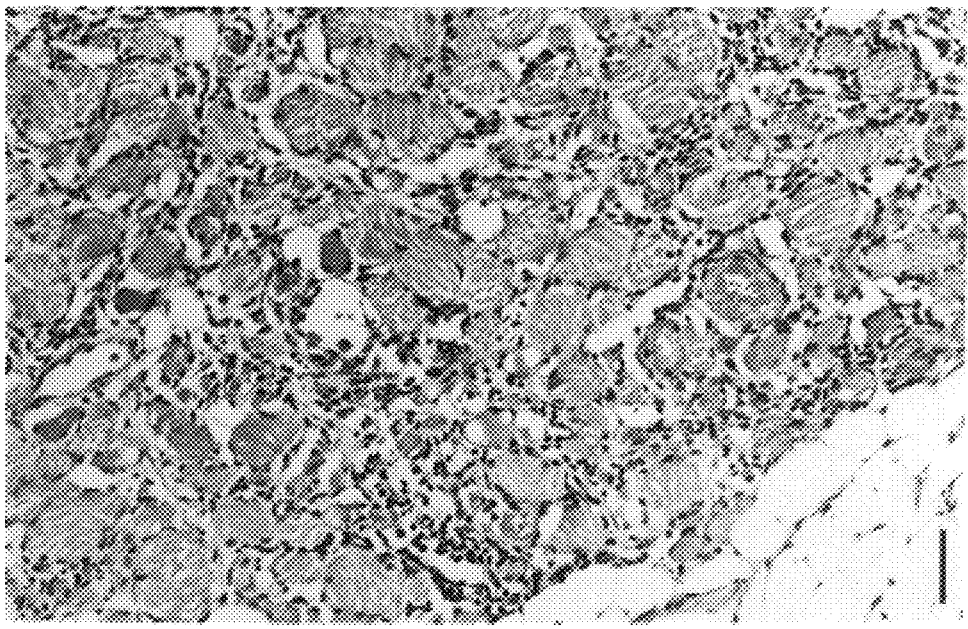

Bar=20 μm;

FIG. 6: Degeneration of aerobic (red) skeletal muscle showing increased endomysial connective tissue, proliferation of sarcolemmal cells and hyaline degeneration of muscle fibres at post-inoculation day 21

Bar=50 μm; and

Figure 7:
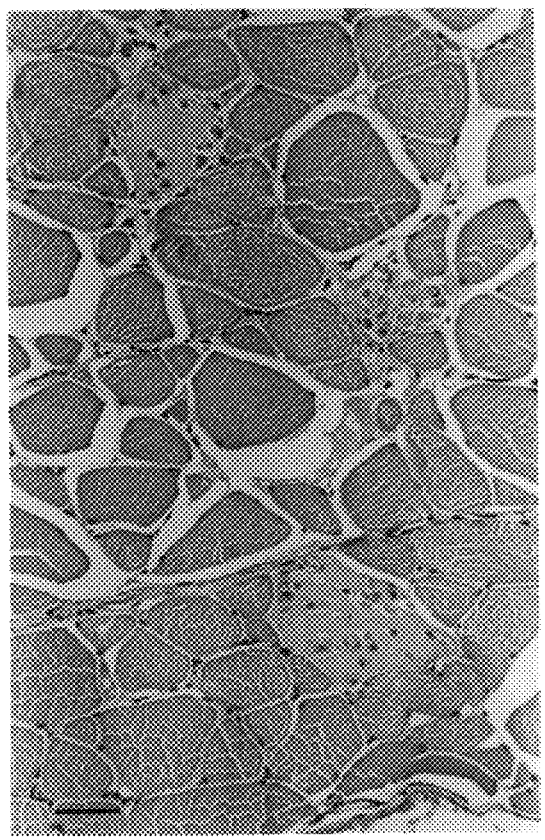

FIG. 7: Hyaline degeneration of anaerobic (white) skeletal muscle fibres showing centralisation of muscle fibre nuclei and phagocytosis of fibre contents Bar=50 μm.

Figure 8A:
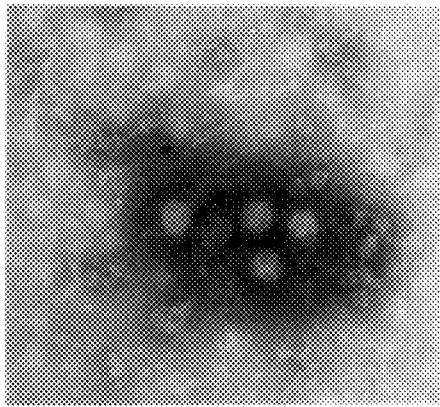
Figure 8B:
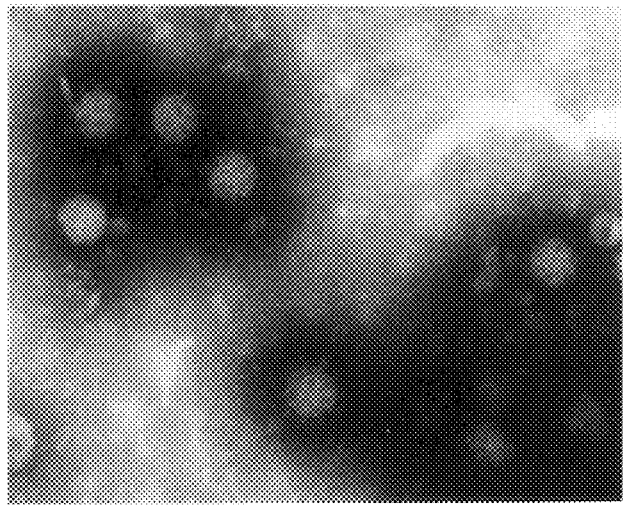

FIG. 8: Virus Isolate×100,000

The present invention will now be further described with reference to the following, non-limiting, examples.

EXAMPLE 1

Isolation and Cell Culture of Virus

Cell Cultures

For virus isolation the chinook salmon embryonic cell line (CHSE-214, Nims et al, 1970) was used throughout the investigation. Other cell lines used include epithelioma papulosum cyprini (EPC), fathead minnow (FHM), bluegill leponis macrochirus (BF2), Atlantic salmon (AS), rainbow trout gonad (RTG-2) and rainbow trout fibroblast (RTF) cells. Cells were maintained in Eagle's minimum essential medium (MEM) containing Earle's salts and sodium hydrogen carbonate 2.2 g/l supplemented with 200 mM L-glutamine, 1% non-essential amino acids, 0.01M Hepes, penicillin 100 IU./ml, streptomycin 100 µg/ml and 10% foetal bovine serum (FBS) Gibco, Scotland. Cells were propagated in either 150 cm² flasks or 24 well plates (Costar 3524) at 20° C.

Plates were incubated in closed containers in 3% $CO_2$/97% air atmosphere. For maintenance of cells during virus isolation, a maintenance medium (MEMM) was used comprised of MEM with antibiotics increased as follows; penicillin 500 IU $ml^{-1}$, streptomycin sulphate 500 µg $ml^{-1}$, amphotericin B 0.625 µg $ml^{-1}$; and FBS was reduced to 2%.

Original Virus Isolation

Samples of kidney, spleen, heart, liver, pancreas and gut were taken from 20 individual fish during the acute phase of an outbreak of Pancreas disease in farmed Atlantic salmon on the west coast of Ireland. Samples from each fish were treated separately.

Co-cultivation

For isolation attempts by co-cultivation, half portion aliquots of each kidney were fragmented by placing them in a 2 ml syringe and forcing them through a 16 gauge hypodermic needle into 10 ml of maintenance medium (MEMM). The suspension of tissue pieces obtained were inoculated into monolayers of CHSE-214 cells prepared 24 hours previously. One ml of the tissue suspension was inoculated into each well of a 24 well plate and incubated at 15° C. for 28 days or until a cytopathic effect (CPE) was observed, when passage into CHSE cells, without freezing and thawing, and incubation for a further 28 days was carried out.

Tissue Homogenates

The remaining kidney portions and other tissues from each fish were pooled and 10% homogenates prepared with MEMM using a pestle and mortar. These were centrifuged at 2500 g for 15 minutes and 0.1 ml of the supernatants were inoculated at final dilutions of 1:20, 1:50 and 1:100 in MEMM into 24 well plates containing CHSE-214 cells. These were incubated at 15° C. for up to 28 days or until the appearance of CPE, when passage into CHSE cells and incubation at 15° C. to a further 28 days was carried out.

Viral Growth Curve in CHSE-214 Cells

Virus growth in CHSE-214 cells was measured by inoculation of 0.1 ml of FPDV on to CHSE-214 cells in 24 well plates at a multiplicity of infection (MOI) of 1 $TCID_{50}$/cell and allowing virus to absorb for 1 hour at 15° C. The innoculum was removed and the cells washed three times with MEMM, before replacing with 1 ml MEMM. Samples were removed for assay on postinoculation days (PID) 0, 2, 4, 6, 8, 10, 12, 14, 21 and 28 as follows. For extra-cellular virus samples, half of the culture medium was removed from each of 4 wells, pooled and centrifuged at 800×g for 5 minutes to remove the cells. The supernatant contained extra-cellular virus. For total virus samples, the remaining 0.5 ml of culture medium, along with the adherent cells removed by scraping, were pooled, and frozen and thawed once. Both samples were assayed separately for virus infectivity by titration in CHSE-214 cells incubated at 15° C. for 14 days. The 50% end points in this and all subsequent tests were estimated by the method of Reed and Muench (1938) Am. J. of Hygiene 27: 493–497.

Growth of the virus in cell cultures

Examinations for cytopathic effects of FPDV in epithelioma papilloma cyprini (EPC), fathead minnow (FHM), bluegill leponis macrochirius (BF2), Atlantic salmon (AS) (Flow, Scotland) rainbow trout gonad (RTG) cells and a rainbow trout fibroblast cell (RTF) line produced in this laboratory were carried out. Cultures were inoculated with ten-fold dilutions of a virus pool containing $10^7$ $TCID_{50}$ $ml^{-1}$, incubated at 15° C. and examined for evidence of CPE over 14 days. Any CPE was noted and cultures were tested for virus growth by titration of culture fluids in CHSE-214 cells. All cultures were given one further passage for 14 days in the same cells at 15° C., and checked again by virus growth in CHSE-214 cells before discarding.

RESULTS

Virus Isolation

Virus was isolated from two out of twenty kidney tissues submitted for examination. These had been co-cultivated with CHSE-214 cells for 28 days and then given further passages in CHSE-214 cells. No CPE was seen in the original co-cultivation cultures. On passage however, small discrete groups of cells which were pyknotic, vacuolated and irregular in appearance could be observed after 10 days incubation. After four further passages in CHSE-214 cells the CPE had become widespread (see FIG. 1). Virus titres of $10^{8.5}$ $TCID_{50}$/ml were routinely obtained. Most of the affected cells remained attached to the monolayers. No syncytia or inclusion bodies were observed in any of the cultures. No virus was isolated from any of the tissue homogenates inoculated.

Description of Cytopathic Effects in CHSE-214 Cells

In the early passages small discrete groups of cells became pyknotic, vacuolated and irregular in appearance. These increased over three weeks until up to the three-quarters of the monolayer became affected. Infected cells did not detach from the surface of the culture plate. When the virus became cell adapted the CPE appeared as early as 4 days and were usually complete by 14 days.

Growth in Various Call Cultures

Growth of the virus in CHSE-214 cells is shown in FIG. 2. Highest total virus levels were achieved by 6–8 days post-inoculation, whereas extra-cellular virus peaked around 11 days post-inoculation and remained high for up to 14 days post-inoculation. No CPE were observed in AS, BF2, FHM, EPC, or RTG-2 cells and there was no evidence of growth of FPDV in these cells. However, in the RTF cell line although no CPE were observed, FPDV titres reached $10^6$ $TCID_{50}$ $ml^{-1}$ on both first and second passage in these cells.

EXAMPLE 2

Chloroform Sensitivity

Sensitivity to chloroform was determined by adding 0.05 ml chloroform to 1 ml of virus. The mixture was shaken for 10 minutes at ambient temperature then centrifuged at 400×g for 5 minutes to remove the chloroform. Residual infections virus was detected by titration in CHSE-214 cells. A control consisted of 0.05 ml of MEMM added to 1 ml of virus instead of chloroform. Infectious Pancreatic Necrosis Virus (IPNV) and Viral Haemorrhagic Septicaemia virus (VHS) were also included as negative (non-sensitive) and positive (sensitive) virus controls respectively.

RESULTS

The infectivity of the isolate and VHS virus was reduced following exposure to chloroform indicating the presence of an envelope containing essential lipids.

TABLE 1

Sensitivity of FPDV to chloroform
Virus concentration Log $TCID_{50}/ml$

| Virus | Control | Treated |
|---|---|---|
| FPDV | 7.5 | <1.0 |
| IPNV | 7.5 | 7.5 |
| IHN | 6.0 | <1.0 |

In contrast IPNV infectivity was not affected when treated in the same way.

EXAMPLE 3
Stability at pH 3.0

Stability at pH 3.0 was determined by adding 0.1 ml virus to 0.9 ml MEM adjusted to pH 3.0, holding for 4 hours at 4° C. then checking for residual infections virus by titrating in CHSE-214 cells at 15° C. for 14 days. The experiment was repeated with FPDV added to MEM at pH 7.2 as a control. IPNV was included as a pH 3.0 stable virus control and infectious hematopoietic necrosis virus (IHN) was used as a pH 3.0 sensitive control

RESULTS

TABLE 2

Sensitivity of FPDV to pH 3.0
Virus concentration Log $TCID_{50}/ml$

| VIRUS | pH 3.0 | pH 7.2 |
|---|---|---|
| FPDV | <1.0 | 6.5 |
| IPNV | 7.5 | 7.5 |
| IHN | <1.0 | 6.0 |

The infectivity of the isolate was lost when it was exposed to pH 3.0. IPNV was not affected.

EXAMPLE 4
Temperature Stability

Aliquots of viral suspension were heated for 30 minutes at 15, 25, 37, 45, 50, 55 or 60° C. and then cooled immediately by immersion in iced water. The concentration of infectious virus remaining was assayed by titration in CHSE-214 cells incubated at 15° C. for 14 days.

RESULTS

The infectivity was not affected at 4, 15, 25° C. but was reduced at 37 and 45° C. No infectious virus was detected after 30 minutes at 50° C.

Table 3
Stability of FPDV held at different temperatures for 30 minutes. Residual virus assayed for infectivity in CHSE-214 cells, incubated at 15° C. for 14 days.

| Temp (° C.) | Virus concentration Log $TCID_{50}/ml$ |
|---|---|
| 4 | 7.5 |
| 15 | 7.5 |
| 25 | 7.5 |
| 37 | 6.5 |
| 45 | 5.5 |
| 50 | — |

EXAMPLE 5
Haemagglutination

Tests for haemagglutination were carried out with chicken, guinea pig, rainbow trout, and Atlantic salmon erythrocytes is U-bottomed 96 well plates, by adding 0.1 ml of a 0.8% suspension of red blood cells in phosphate buffered saline (PBS) pH 7.2 to 0.1 ml of a FPDV pool prepared in CHSE-214 cells with a titre $10^7$ $TCID_{50}/ml$ and incubating at 4° C., 15° C., and 37° C. Tests were examined after 1, 3 and 18 hours.

RESULTS

No haemagglutination was observed at any of the temperatures, or with any of the eythrocytes selected.

EXAMPLE 6
Nucleic Acid Inhibition Test

The nucleic acid type of the virus was determined by growing the virus in the presence of the DNA inhibitor 5-bromo-2'-deoxyuridine (BUDR) with and without thymidine. Groups of 4 wells in each of three 24-well plates containing CHSE-214 cells were inoculated with 0.1 ml of ten-fold dilutions of virus, which were allowed to absorb for 1 hour at 15° C. To each plate 1 ml of MEMM alone, MEMM with 1 mM/ml BUDR or MEMM with 1 mM/ml BUDR and 1 mM/ml thymidine, were added. The plates were incubated at 15° C. for 14 days and examined for CPE. A fish RNA virus (IPN) and a DNA virus (lymphocystis) grown in BF2 cells were included as controls.

RESULTS

TABLE 4

Replication of FPDV in CHSE-214 cells in the presence of 1mM 5-bromo-2'-deoxyuridine (BUDR)
Virus concentration Log $TCID_{50}/ml$

| Virus | MEMM | MEMM + BUDR | MEMM + BUDR + THY |
|---|---|---|---|
| FPDV | 7.0 | 7.25 | 7.0 |
| IPNV | 7.5 | 7.25 | 7.5 |
| Lymphocystis virus | 7.2 | 5.0 | 7.0 |
| IHN | 6.0 | nd | nd | nd = Not done

The virus titre of the isolate and IPNV was not affected by the presence of BUDR in the medium whereas the fish DNA virus was inhibited. This indicates that the genome of the isolate is comprised of RNA.

EXAMPLE 7
Negative Contrast EM Examination

Virus suspensions for EM examinations consisted of either FPDV infected cell culture medium used without prior fixation or after the addition of glutaraldehyde (2% final conc.) for 1 hour at 4° C. and subsequent ultracentrifugation at 100 000×g for 4 hours, then resuspension of the pellet in a few drops of distilled water. A carbon coated copper grid was placed on top of a drop of virus suspension and allowed to stand for 10 minutes. Excess fluid was drained off and the grid was stained with 2% phosphotungstic acid (PTA) (pH 7.2) for 1 minute. It was examined in a Hitachie H7000 transmission EM at ×50,000 magnification.

RESULTS

Virus preparations not fixed in glutaraldehyde before EM examination contained mostly disrupted particles. indicating that pre-fixation is required to preserve the intact virion.

Figure 1A:
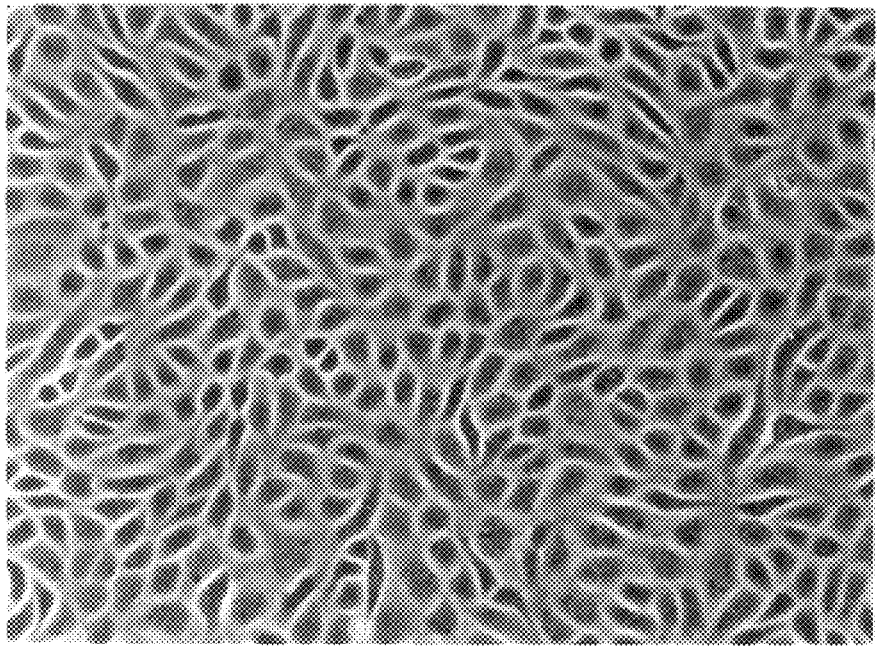
FIG. 1a: Uninfected CHSE-214 cells (Magnification× 750)
Figure 1B:
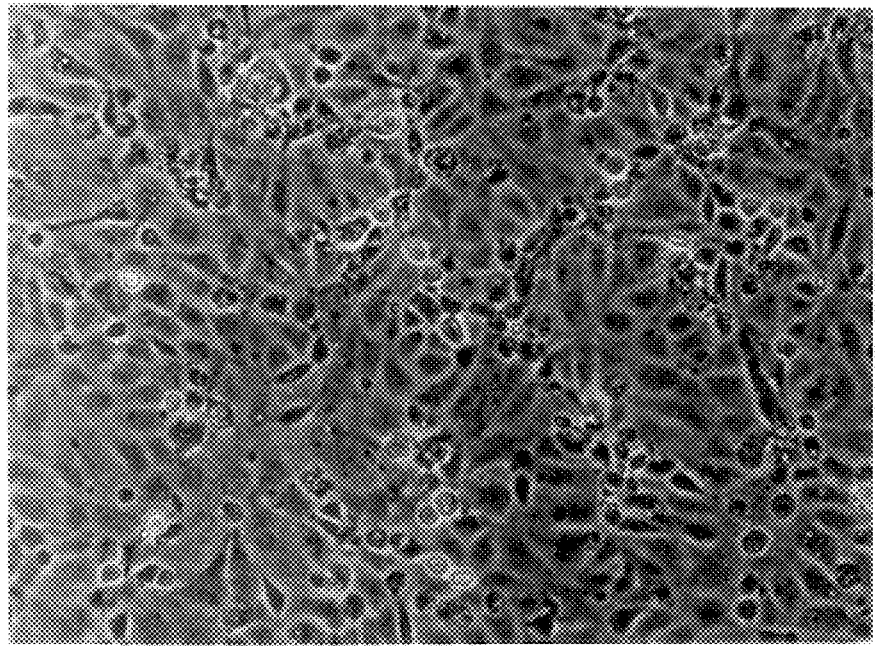
FIG. 1b: CHSE-214 cells, 8 days post-inoculation with FPDV (Magnification×750)
Figure 3:
FIG. 3: Transmission electron micrographs of glutaraldehyde fixed, FPDV infected CHSE-214 cell culture fluid. Most of the virus particles have surface projections, but little internal structure detail Bar=100 nm.
Figure 4:
FIG. 4: Significant pancreatic acinar cell loss, typical of pancreatic lesions induced by FPDV at post-inoculation day 21

EM examination of the glutaraldehyde fixed material revealed the presence of circular particles measuring 65.5±4.3 nm (FIG. 3). These possessed an inner core of indefinite structure and were surrounded by an outer fringe of what appeared to be club-like projections. Many partially disrupted particles were also present. In the unfixed preparations only a few complete particles were seen and this indicates that the free virion is fragile and easily disrupted during preparation for EM examination.

EXAMPLE 8
Growth and Concentration of Virus
Growth of Virus in CHSE-214 Cells Virus growth in CHSE-214 cells was measured by inoculation of 0.1 ml of FPDV on to CHSE-214 cells in a 24 well plate at a multiplicity of 1.0 $TCID_{50}$/cell and allowing it to absorb for 1 hour at 15° C. The virus was then removed and the cells washed twice with MEMM before replacing with 1 ml MEMM. Samples were removed for assay on days 0, 7, 11, 14, 21, 28 post inoculation as follows. Half of the culture medium was removed from each of 4 wells pooled and centrifuged at 800×g for 5 minutes to remove the cells. The remaining 0.5 ml of culture medium along with the adherent cells, removed by scraping were pooled, and then frozen and thawed once. Both samples were assayed separately for virus infectivity by titration in CHSE-214 cells at 15° C. for 14 days.

Caesium Chloride Gradient Centrifugation

FPDV was inoculated into CHSE-214 cells at an MOI of 1. Cells and medium (400 ml) were harvested at 8 days post inoculation and frozen and thawed once at −70° C. before centrifugation at 10,000×g for 30 minutes in a Beckman Type 35 angle rotor to remove cell debris. The supernatant was subjected to ultracentrifugation of 100,000×g for 4 hours. The resultant pellet was resuspended in a total of 2 ml of PBS pH 7.2 and layered over a discontinuous CsCl gradient comprised of 5 ml of 1.3 g/ml CsCl and 4.5 ml of 1.22 g/ml CsCl. This was centrifuged at 100,000×g for 19 hours at 4° C. 20 fractions were collected and tested for infectivity in CHSE-214 cells incubated at 15° C. for 14 days. The density of the fractions containing infective virus was determined using a refractometer.

RESULTS

Infectivity was detected in fractions from CsCl gradients with densities from 1.08 to 1.26 g/ml. The maximum infectivity was observed at a density of 1.2 g/ml and this fraction also contained the greatest number of complete virus particles as assessed by EM examination.

EXAMPLE 9

Serological Tests

FPDV was tested for neutralisation by hyperimmune rabbit sera against Infectious Haematopoietic virus (IHN), Viral Haemorrhagic Septicaemia virus (VHS), Infectious Pancreatic Necrosis virus, strains Sp, Ab, and VR-299 (IPNV), Equine arteritis virus (EAV), Bovine Viral Diarrhoea virus (BVD), and Rubella virus. Equal volumes of 200 $TCID_{50}$/0.1 ml of FPDV was added to 0.1 ml of two-fold dilutions of antisera and incubated at 15° C. for 1 hour. The mixtures were then inoculated into CHSE-214 cells in 24 well plates, 0.1 ml per well, allowed to absorb for 1 hour, 1 ml MEMM added and incubated at 15° C. for 14 days, and the cultures examined microscopically on alternate days for evidence of CPE. Titres were calculated by the method of Reed and Meunch, 1938 in Amer. J. of Hygiene 27:493–497.

RESULTS

FPDV was not neutralised by antisera to IHNV, VHSV, IPNV, EAV, BVD or Rubella, indicating that it was not related to these virus groups.

EXAMPLE 10

TRANSMISSION EXPERIMENT

1) Materials and Methods a) Fresh-water Fish

Atlantic salmon parr of mean weight 20 g±2.9 g were maintained in circular 1.2 m diameter tanks containing liters of partially re-circulated spring source water at 10–12° C. The fish were kept in these tanks for 2 weeks prior to inoculation to acclimatise and were fed on a commercially prepared diet to satiation. Tissues were removed from 10 fish and examined for the presence of Infectious Pancreas Necrosis virus (IPNV) and Pancreas Disease. Before inoculation fish were anaesthetised with 3-aminobenzoic acid ethyl ester (MS222).

b) Marine Fish

Atlantic salmon post-smolts of mean weight 87 g were maintained in 2×1.5 m tanks containing sea water in a flow through system at 12–15° C. They were kept for 2 weeks to acclimatise prior to inoculation, and samples of tissue from 10 fish were cultured for the presence of IPNV and examined histologically for evidence of Pancreas disease.

2) Experimental Procedures

Inoculum 1

A FPDV pool was prepared by inoculating virus into CHSE-214 cells at a multiplicity of infection of 1 $TCID_{50}$ per cell and harvesting after 8 days incubation at 15° C. The cells were disrupted by freezing and thawing once at −70° C. and the cell debris was removed by centrifugation at 10,000×g for 30 minutes. The resultant virus pool, titre $10^{7.0}$ $TCID_{50}$/ml was filtered through a 0.22 micron porosity Millipore filter and 0.1 ml inoculated intraperitoneally into each of 100 fish. Fifty fin-clipped un-inoculated fish were added to each of the tanks as in-contact fish.

Inoculum 2

As controls 100 fish were inoculated with a lysate from un-infected CHSE-214 cells prepared in exactly the same manner as the virus infected cells, and 50 additional in-contact control fish were added.

Sampling

On days 6 or 7, 10, 14 or 15, 21, 28, 35, 42 post-inoculation, samples of heart, spleen, kidney, liver, caecae/pancreas and muscle were taken from 10 test and 10 control fish for histological examination. Heart, spleen, kidney and caecae/pancreas samples were also taken from the same fish for virus isolation until day 28. At days 14 or 15, 21, 28, 35 and 42 post-inoculation 5 in-contact fish were removed and tissues sampled for histological examination. In-contact fish were sampled for virus isolation on days 14 or 15 and 21 only.

Histology

Samples for histological examination were fixed in 10% formaldehyde in buffered saline pH 7.0, embedded in paraffin wax and 5 micron sections cut on a Reichert Ultracut S microtome. These were stained with haematoxylin and eosin.

Virus isolation

Tissues were prepared as 10% homogenates in MEMM, using mortars and pestles, centrifuged at 2,500×g for 15 minutes then inoculated at final dilutions of 1:20 and 1:10 into each of 2 wells in a 24 well plate containing CHSE-214 cells and incubated at 15° C. for 28 days. Samples showing no CPE were given one further passage into CHSE-214 cells before being considered negative.

RESULTS

Clinical and Pathological Lesions in Freshwater Salmon Parr

When the virus was inoculated into freshwater salmon parr, some of the parr stopped feeding and faecal casts were observed. Acute pancreatic acinar necrosis was detected from 6–10 days post inoculation (p.i.). The necrosis was focal to diffuse in distribution. Between day 14 and 21 many of the fish had significant acinar loss but pockets of surviving acinar tissue were detected especially around the islets of Langerhans and larger intralobular ducts in some fish. There was mild fibrosis of the periacinar tissue. Concurrent multifocal myocytic necrosis and degeneration was detected from day 6 p.i. in all fish with pancreatic lesions. In week 3 post-inoculation the hearts appeared hypercellular with apparent proliferation of myocytic and sub-endocardial cells with myocytic nuclear enlargement. Mild skeletal muscle lesions were detected from 21 days p.i. In contact fish developed similar lesions after a 2 week delay. No histological lesions were detected in the negative controls.

Clinical and Pathological Lesions in Seawater transmission experiment

By day 7, the fish inoculated with FPDV became anorexic and there was an increase in faecal casts in the tank. Focal to severe diffuse acinar cell necrosis with concurrent multifocal cardiomyocytic necrosis was consistently observed from day 7. Skeletal muscle fibre degeneration was detected from day 15, affecting both red and white skeletal muscle fibres. These muscle lesions increased in frequency and severity at days 35 and 42. Typical lesions observed at day 21 are illustrated in FIGS. 4 to 7. All the cohabitant fish developed similar lesions after a 2 week delay. No clinical signs or lesions were detected in any of the control fish.

Isolation of Virus in Transmission Experiments

Virus was isolated from all tissues of the inoculated fish, but at different times post-inoculation (Table 5), with the heart tissue giving the best success rate.

TABLE 5

Transmission Experiment - Fresh-water fish.
Virus isolations from 10% tissue homogenates inoculated into CHSE-214 cells and incubated at 15° C. for 14 days.

| Tissue | Days post-inoculation | | | | |
|---|---|---|---|---|---|
|  | 6 | 10 | 14 | 21 | 28 |
| kidney | + | + | + | + | − |
| spleen | − | + | + | − | − |
| heart | + | + | + | + | + |
| pancreas | − | − | + | + | + |
| liver | − | + | + | − | − |
| gut | − | + | + | + | + |

In contact fish from the same tank became infected with the virus, although none of the control fish were found to contain virus. The results for the sea-water fish are given in Table 6. No IPN virus was detected at any stage in the transmission study.

TABLE 6

Virus isolation in transmission experiment (sea-water fish)

| Fish | Number positive/number examined Days post-inoculation | | | | |
|---|---|---|---|---|---|
|  | 7 | 10 | 15 | 21 | 28 |
| Inoculated controls | 0/10 | 0/10 | 0/10 | 0/10 | 0/10 |
| Virus inoculated | 7/10 | 8/10 | 10/10 | 3/10 | ND* |
| Not inoculated (in-contacts) | ND* | ND* | 5/5 | 5/5 | ND* |

ND* = Not Done

Summaries of the histological results are shown on Table 7 and 8.

TABLE 7

Summary of Histological Findings in Experimental Transmission Studies Using FPDV in Fresh-water Fish

| Tissue | Days post infection | | | | |
|---|---|---|---|---|---|
|  | 4 | 7 | 14 | 21 | 28 |
| Pancreas | − | + 7/10 | + 10/10 | + 10/10 | + 2/10 |
| Heart | − | + 7/10 | + 10/10 | + 9/10 | + 2/10 |

No lesions detected in any negative controls

TABLE 8

Summary of Histological Findings in Experimental Transmission Studies using FPDV in Seawater Salmon Smolts

| Tissue | Days post infection | | | | |
|---|---|---|---|---|---|
|  | 7 | 10 | 15 | 21 | 28 |
| Pancreas | + 9/10 | + 10/10 | + 10/10 | 10/10 | 9/10 |
| Heart | + 6/10 | + 10/10 | + 10/10 | 10/10 | 6/10 |
| Muscle | 0 | 0 | 2/10 | 8/10 | 9/10 |

No lesions detected in any negative controls.

EXAMPLE 11

INACTIVATED FISH PANCREAS DISEASE VIRUS (FPDV) VACCINE

Experimental Protocol

AIM OF STUDY

To investigate if inactivated FPDV with added adjuvant, when inoculated into salmon parr, can protect the fish from challenge with live FPDV.

Materials and Methods

Virus used in Preparation of the Vaccines

11th passage FPDV was grown in CHSE cells and harvested at 6 days post inoculation and centrifuged at 1000×g for 15 minutes 600 ml of the resulting supernatant was passed through an Amicon filter producing 25 ml of concentrated FPDV at a titre of $10^{7.5} TCID_{50}\ ml^{-1}$.

Virus Inactivation Method
  A. 10 ml FPDV as prepared above +0.2% beta-propiolactone (BPL)+2 drops NaOH B. 10 ml FPDV as prepared above +0.1% formalin (35–38%)

C. MEMM (maintenance medium).

Aliquots of A, B and C were stored at +4° C. for 24 hours before addition of a suitable adjuvant. Adjuvant was added after virus was inactivated and both virus and control were received and inoculated into fish 8 days after initial inactivation.

Vaccination Protocol

FISH:Salmon parr, average wt 27 g, were kept in freshwater flow-through system for 1 or 2 weeks pre-vaccination. (Water temperature range 10–14° C.).

Blood and tissue samples were taken from 5 fish per group prior to vaccination.

0.1 ml of inactivated-adjuvanted FPDV as prepared in A and B and the adjuvant control group C (MEMM plus adjuvant) was inoculated intraperitoneally (I/P) into 50 fish per group.

Sampling 10 fish from each group were sampled 1 week before challenging with FPDV.

Bloods and histopathological samples were taken and checked for evidence of pancreas disease (PD).

No evidence of PD was found histologically or by virus isolation.

Challenge Protocol 0.1 ml of live $10^{4.5}$ $TCID_{50}$ $ml^{-1}$ of 9th passage FPDV was inoculated I/P into each fish in the 3 test groups at 28 days post-vaccination.

A fourth group D of 50 naive unvaccinated fish, were also inoculated I/P with the same amount of FPDV to act as a positive control.

After 10 and 14 days post challenge, 5 fish were sampled from each group.

Blood samples for antibody tests, kidney and heart tissue samples for virus isolation, and pyloric caeca, heart and muscle samples for histology were taken.

VACCINE EXPERIMENT 1

| Group/ | 10 DAYS | | | 14 DAYS | | | 21 DAYS | | |
|---|---|---|---|---|---|---|---|---|---|
| | Histology | | | Histology | | | Histology | | |
| No | Panc | Heart | Virus | Panc | Heart | Virus | Panc | Heart | Virus |
| A1 | + | + | + | + | + | ND | | | |
| A2 | + | + | | + | + | | | | |
| A3 | + | − | | + | + | | | | |
| A4 | + | − | | + | + | | | | |
| A5 | + | − | | + | + | | | | |
| B1 | − | − | − | − | − | − | − | − | − |
| B2 | − | − | | − | − | | − | − | |
| B3 | − | − | | − | − | | − | − | |
| B4 | − | − | | − | − | | | | |
| B5 | − | − | | − | − | | | | |
| C1 | − | − | + | + | + | ND | | | |
| C2 | + | + | | + | + | | | | |
| C3 | + | − | | + | + | | | | |
| C4 | + | + | | − | − | | | | |
| C5 | + | + | | + | + | | | | |
| D1 | + | + | + | + | + | + | | | |
| D2 | + | + | | + | + | | | | |
| D3 | + | + | | + | + | | | | |
| D4 | + | + | | + | + | | | | |
| D5 | + | + | | + | + | | | | |

-continued

VACCINE EXPERIMENT 1

| Group/ | 10 DAYS | | | 14 DAYS | | | 21 DAYS | | |
|---|---|---|---|---|---|---|---|---|---|
| | Histology | | | Histology | | | Histology | | |
| No | Panc | Heart | Virus | Panc | Heart | Virus | Panc | Heart | Virus |

1 + = lesions or virus present
2 − = no lesions or virus present
3 ND = not done
4 GROUP A = FPDV + 0.2% BPL + ADJUVANT
5 GROUP B = FPDV + 0.1% FORMALIN + ADJUVANT
6 GROUP C = CONTROL MEMM + ADJUVANT
7 GROUP D = UNVACCINATED CONTROLS

EXAMPLE 12

INDIRECT FLUORESCENT ANTIBODY TEST (IFA) FOR DETECTION OF FPDV ANTIGEN IN CELL CULTURES

Introduction

The test involves addition of serum, containing FPDV antibody, to CHSE cells suspected of being infected with the virus. If virus is present the antibody will bind to the antigen present. Anti-salmon IgM prepared in rabbits is then added and will attach to the bound antibody. This attachment is detected by the addition of anti-rabbit serum conjugated to fluorescein isothiocyanate (FITC) which can be viewed as green fluorescence using a fluorescent microscope.

Materials

CHSE-214 cells are grown on 11 mm diameter coverslips in 24-well plates (Costar) by seeding 45,000 cells in 0.5 ml of growth medium (MEM+10% foetal bovine serum) per coverslip. The cultures are incubated at 20° C. in a closed container with 3% $CO_2$/air mixture for 48 hours before use.

Positive serum—convalescent serum from FPDV affected salmon used at 1/50 dilution in phosphate buffered saline (PBS) pH 7.2.

Negative control serum—salmon serum with no antibody to FPDV diluted 1/50 in PBS.

Rabbit anti-salmon IgM—obtained commercially from Soren Schierbeck & Co, Helsingor, Denmark, diluted 1/50 in PBS.

Anti-rabbit Ig/FITC—obtained commercially from Nordic Imm. Labs., Berks, England, diluted 1/1000 in PBS.

Method

Material suspect of containing FPDV is added to the coverslips in wells containing 1 ml MEMM (maintenance medium) and incubated for 5 days at 15°0 C. in a closed container with 3% $CO_2$/air mixture. The coverslips are washed twice in PBS and fixed in acetone for 5 minutes then stored at +4° C. until used. Negative control cultures, without suspect samples, as well as positive control cultures, containing FPDV, are prepared in the same way.

Test and control coverslips are overlaid with 50 $\mu$L of positive and negative sera and incubated at 35° C. for 30 minutes in a humidified 100 mm square petri dish. PBS is added to separate coverslips as reagent controls. All coverslips are then rinsed in PBS for 6 minutes (3 changes of 2 minutes each) and excess PBS is drained off on tissue paper. 50 $\mu$L of anti-salmon IgM is added to all coverslips and incubated for 30 minutes at 35°0 C. Further rinsing is carried out in PBS for 6 minutes and 50 $\mu$L of anti-rabbit/FITC is added to all coverslips which are incubated for 30 minutes at 35°0 C. A final rinsing is carried out for 6 minutes in PBS and the coverslips are examined under a 40× objective on a Labophot 2 fluorescence microscope with the coverslips under buffered glycerol saline pH 9.2. Green fluorescence similar to the positive controls, with absence of fluorescence in the negative controls indicates presence of FPDV antigen in cultures.

EXAMPLE 13

INDIRECT FLUORESCENT ANTIBODY TEST (IFA) FOR DETECTION OF ANTIBODY TO FPDV IN SALMON SERUM

Introduction

The test involves addition of salmon serum to FPDV infected CHSE-214 cells. If antibody to FPDV is present in the serum it will bind to the virus infected cells. Anti-salmon IgM prepared in rabbits is then added to the preparation and will attach to any bound antibody. This attachment is recognised by addition of anti-rabbit serum conjugated to fluorescein thiocyanate (FITC) which can be viewed as green fluorescence (FITC) under a fluorescence microscope.

Materials

FPDV infected cells are prepared by adding virus to CHSE-214 cell suspension containing 200,000 cells per ml, at a multiplicity of 1 and seeding 40 $\mu$L into each well of 12 well multispot slide (Hendley, Essex). The cultures are incubated in a 3% $CO_2$/air atmosphere in a closed container at 20° C. for 24 hours. They are then transferred to a 15° C. incubator and incubated for a further 3 days before rinsing twice with phosphate buffered saline (PBS) pH 7.2, fixing with acetone for 5 minutes and storing at +4° C. until used. Control CHSE-214 cultures without virus are prepared in the same way.

Test sera—salmon serum for antibody testing.

Positive control serum—salmon serum shown to have neutralising antibody by serum neutralising antibody test (SNT).

Negative control serum—salmon serum with no antibody by SNT.

Rabbit anti-salmon IgM—obtained commercially from Soren Shierbeck & Co, Helsingor, Denmark.

Anti-rabbit Ig/FITC—obtained commercially from Nordic Imm. Labs. Berks, England.

Method

FPDV positive and negative multispot wells are overlaid with 30 $\mu$L of salmon test sera diluted 1/20 with PBS pH 7.2. Positive and negative sera at 1/20 dilution in PBS are also included in separate wells. Two wells on each slide also have PBS added as controls and slides are incubated at 35° C. in a humidified 100 $mm^2$ petri dish for 30 minutes. Following rinsing in PBS (three rinses of 2 minutes each) 30 $\mu$L of anti salmon IgM at a 1/50 dilution in PBS is added to all wells and the slides incubated for a further 30 minutes at 35° C. After rinsing for 6 minutes in PBS, 30 $\mu$L anti-rabbit IgM at a 1/100 dilution in PBS is added to each well and the slides incubated for 30 minutes at 35° C. A final rinse in PBS for 6 minutes is carried out and the presence of fluorescence detected using a 40× objective and a Labophot 2 fluorescent microscope with the slides under buffered glycerol saline pH 9.2. A distinctive green fluorescence in test and positive serum wells and not in the controls indicates the presence of antibody to FPDV in these sera. Antibody titrations are carried out using the same method.

EXAMPLE 14

Virus RNA: $^{14}C$ Uridine

Although less commonly use than tritium, this label was chosen because it is detectable using X-ray film.

Labelled, extracelluar virus was pelleted at high speed and extracted for analysis by formaldehyde-gel electrophoresis. In the first experiment, in which Act D was present during labelling period (day 2 to 5), no label was detected on the gel.

RNA present in Act D-treated, infected cells was also investigated. Following extraction by the NP40 lysis method a smear of labelled RNA, increasing in intensity as molecular weight decreased, was observed. No distinctive candidate viral RNAs could be detected.

Larger volumes of extracelluar virus, labelled with $^{14}C$ and $^{3}H$-uridine in the absence of Act D, were pelleted and extracted with the Gensys RNA isolator method. On a formaldehyde gel showing very good resolution of labelled ribosomal RNAs (from infected cells), high-speed pellet virus RNA migrated as a smear. Most of the RNA was of low molecular weight, corresponding in mobility to tRNA or slightly greater, but the smear extended in size to greater than the 5000nt (larger rRNA species). Long exposures of this gel indicated the presence of 2 faint bands, one corresponding in size to the 28S rRNA and the other at a position corresponding to about 10–15 kb. The larger species possesses a mobility similar to that expected for togavirus/flavivirus. One possible explanation for the smaller RNA is that we have detected the subgenomic RNA, produced by togaviruses.

EXAMPLE 15

FISH PACREAS DISEASE VIRUS (FPDV) TRANSFECTION RESULTS

Transfections were successfully performed with (a) RNA extracted from infected CHSE cells (Intracellular RNA), and (b) RNA extracted from virus present in the tissue culture supernatant (Extracellular virus RNA).

RNA Preparation

Intracellular RNA

Monolayers of CHSE cells in 75 $cm^2$ plastic flasks were infected with FPDV (typically $10^4$ $TCID_{50}$). This was done by absorbing the virus contained in 2 ml MEM media for 1 hour and then adding 17 ml media without serum. At 7 days postinfection the media was removed and the cells scraped off the flasks into ice-cold PBS. Cell pellets prepared by centrifugation at 1500 g for 5 minutes, were extracted using “RNA Isolator” (Genosys). Typically, cells from 2 flasks were extracted with 1 ml extraction reagent.

(b) Extracellular virus RNA

Supernatant medium (usually 700–900 ml volumes) from infected CHSE cells was concentrated 5 or 6 fold by Amicon filtration and ultracentrifugation at 35000 rpm for 4 hours using the Beckman 8×70 ml fixed angle rotor to produce crude virus pellets, which were shown to contain high titres of virus infectivity. Typically crude virus pellets derived from 300–450 ml supernatant were extracted with 1 ml “RNA Isolator” reagent.

Transfection

RNA pellets were centrifuged after storage in EtOH at −20° C. at 12000 g for 10 minutes and dissolved in 20 $\mu$l RNAase free water T.ypically, Intracellular RNA derived from the cells contained in approximately 0.25 flask monolayer and Extracellular virus RNA derived from 50–100 ml supernatant were used. Transfection was performed with the “Lipofectin” (Gibco BRL) reagent using the method recommended by the manufacturers. Briefly, this involved mixing RNA solutions with tissue culture media containing Lipofectin and then incubating semiconfluent CHSE cells, grown in 24 well Costar plates, with the mixture (100 μl/1.5 cm diameter well culture) for 5 to 6 hours before replacing the reagent transfection mixture with maintenance medium. Cultures were examined for cpe at daily intervals. Occasionally viral cpe was observed after 4 to 6 days following the subculture of transfected cultures, the subculturing procedure usually being performed 8 days after the transfection.

We claim:

1. As isolated Fish Pancreas Disease Virus (FPDV) that causes Pancreas Disease (PD) in fish.

2. The virus as claimed in claim 1, which is the strain deposited at ECACC under Deposit No. V94090731.

3. The virus as claimed in claim 1, which is free of other viral or microbial material.

4. A vaccine to protect fish against Pancreas Disease, said vaccine comprising an inactivated virus as claimed in claim 1.

5. The virus of claim 1, which is inactivated.

6. An isolated antibody that will bind selectively to a virus as claimed in claim 1 or to a component thereof.

7. The antibody as claimed in claim 6 having a detectable marker.

8. The antibody as claimed in claim 6, which is in immobilized form.

9. A method of diagnosing Fish Pancreas Disease in a fish, said method comprising the following steps:
   1) contacting a test sample with a diagnostic reagent as claimed in claim 6 to produce a reagent complex; and
   2) determining the presence or the concentration of reagent complex and thus the presence or amount of virus in the test sample.

10. A method as claimed in claim 9, wherein the test sample is a blood or a sample of the water in which the fish has been contained.

11. The method of claim 9, further comprising a washing step after step 1) and before step 2).

12. A method of isolating a virus as claimed in claim 1, said method comprising identifying fish suffering from Pancreas Disease, co-cultivating affected tissues with Chinook salmon embryo cells; passaging the co-cultivated cells through Chinook salmon embryo cells; and isolating the virus particles.

13. A method as claimed in claim 12 in which the affected tissues are the pancreas or kidney, and co-cultivation with Chinook salmon embryo cells is undertaken for a period of approximately 28 days.

* * * * *